United States Patent
Olsen et al.

(10) Patent No.: US 6,589,221 B1
(45) Date of Patent: Jul. 8, 2003

(54) COLLECTING BAG FOR HUMAN BODY WASTES

(75) Inventors: Hans Olsen, Hørsholm (DK); Lars Bo Poulsen, Helsingør (DK); Birte Vestbo Anderson, Espergærde (DK); Søren Hansen, Helsingør (DK); Martin Von Bulow, Espergærde (DK)

(73) Assignee: Coloplast A/S, Humlebaek (DK)

( * ) Notice: Subject to any disclaimer, the term of this patent is extended or adjusted under 35 U.S.C. 154(b) by 139 days.

(21) Appl. No.: 09/335,264

(22) Filed: Jun. 17, 1999

(30) Foreign Application Priority Data

Jun. 19, 1998 (DK) ........................................ 1998 00804

(51) Int. Cl.[7] .................................................. A61F 5/44
(52) U.S. Cl. .................................................... 604/332
(58) Field of Search ................................. 604/327, 332, 604/336, 338, 339, 337, 277, 317

(56) References Cited

U.S. PATENT DOCUMENTS

| | | | |
|---|---|---|---|
| 3,507,282 A | | 4/1970 | Burding ........................ 128/283 |
| 3,570,490 A | * | 3/1971 | Berger ......................... 128/283 |
| 3,690,320 A | | 9/1972 | Riely |
| 3,825,005 A | | 7/1974 | Fenton |
| 4,439,191 A | * | 3/1984 | Hogan .......................... 604/332 |
| 4,460,359 A | * | 7/1984 | Fenton ......................... 604/277 |
| 4,465,486 A | * | 8/1984 | Hill ............................... 604/337 |
| 4,561,858 A | * | 12/1985 | Allen, Jr. et al. ............ 604/336 |
| 4,685,990 A | * | 8/1987 | Ferguson ..................... 156/253 |
| 4,755,177 A | | 7/1988 | Hill |
| 4,869,725 A | * | 9/1989 | Schneider et al. .......... 604/408 |
| 4,941,869 A | * | 7/1990 | D'Amico ..................... 604/328 |
| 4,983,172 A | * | 1/1991 | Steer et al. .................. 604/332 |
| 4,988,343 A | * | 1/1991 | Ballan ......................... 604/332 |
| 5,248,308 A | * | 9/1993 | von Emster ................. 604/337 |
| 5,470,325 A | * | 11/1995 | Fundock ...................... 604/333 |
| 5,938,647 A | * | 8/1999 | Smith .......................... 604/332 |
| 5,968,023 A | * | 10/1999 | Olsen .......................... 604/334 |
| 5,968,024 A | | 10/1999 | Freeman ..................... 604/334 |

FOREIGN PATENT DOCUMENTS

| | | |
|---|---|---|
| EP | 0 013 109 | 7/1980 |
| GB | 2 000 683 | 1/1979 |
| GB | 2 268 065 | 1/1994 |
| WO | WO96/19164 | 6/1996 |

* cited by examiner

*Primary Examiner*—Weilun Lo
*Assistant Examiner*—Michele Kidwell
(74) *Attorney, Agent, or Firm*—Jacobson Holman PLLC

(57) ABSTRACT

The collecting bag comprises a bag member (1) formed by two film blanks with joined edges, an inlet opening being provided in one of said film blanks surrounded by connecting elements for connection of the bag to a body orifice. The bag is emptied through a narrowed, elongated discharge portion (8) ending in a discharge opening (9). Sealing plates (35*a*,35*b*) made from a resilient material, eg. foam, are attached to the discharge portion (8) at or near the discharge opening (9) to close the discharge opening by folding of the discharge portion (8).

14 Claims, 5 Drawing Sheets

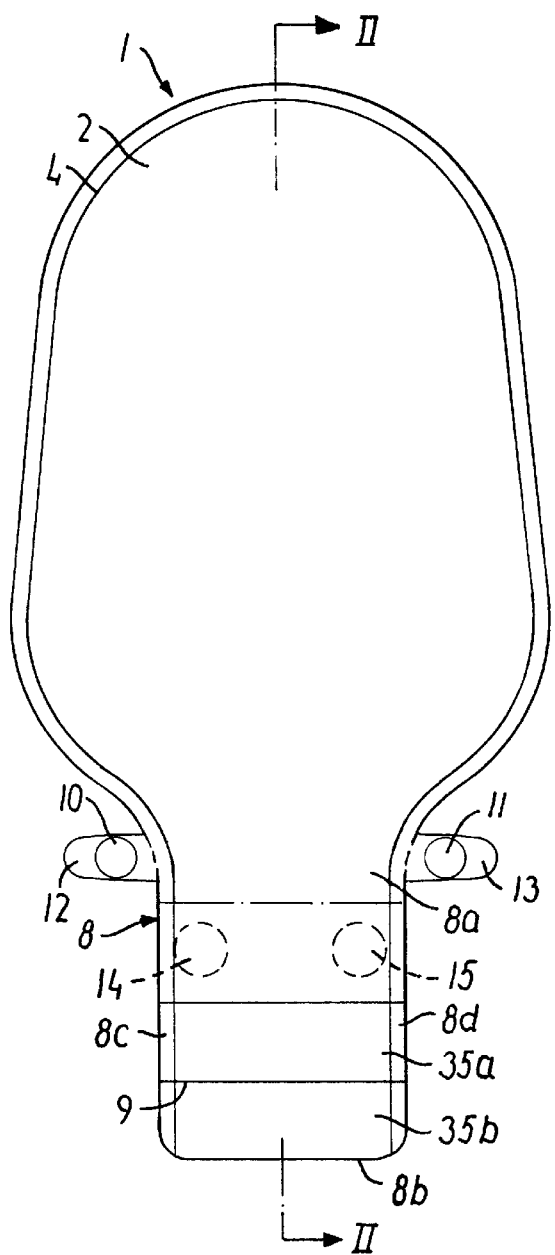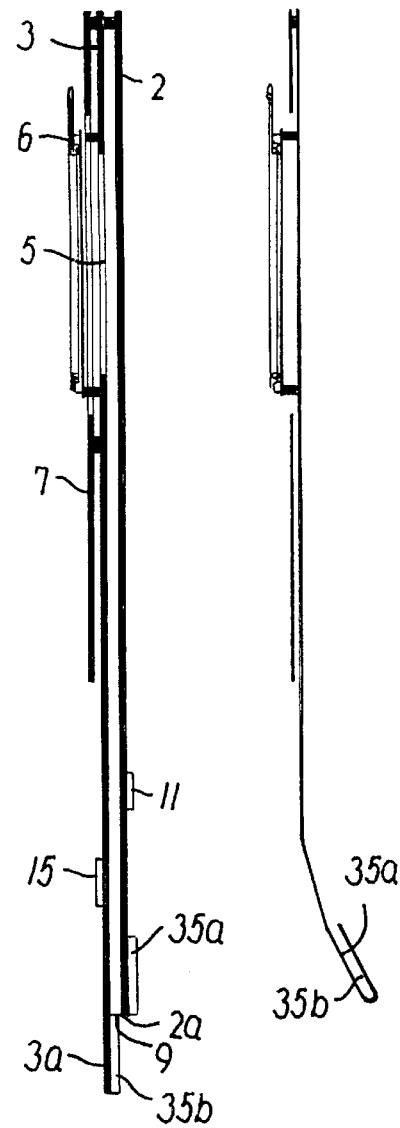
FIG.1   FIG.2   FIG.3

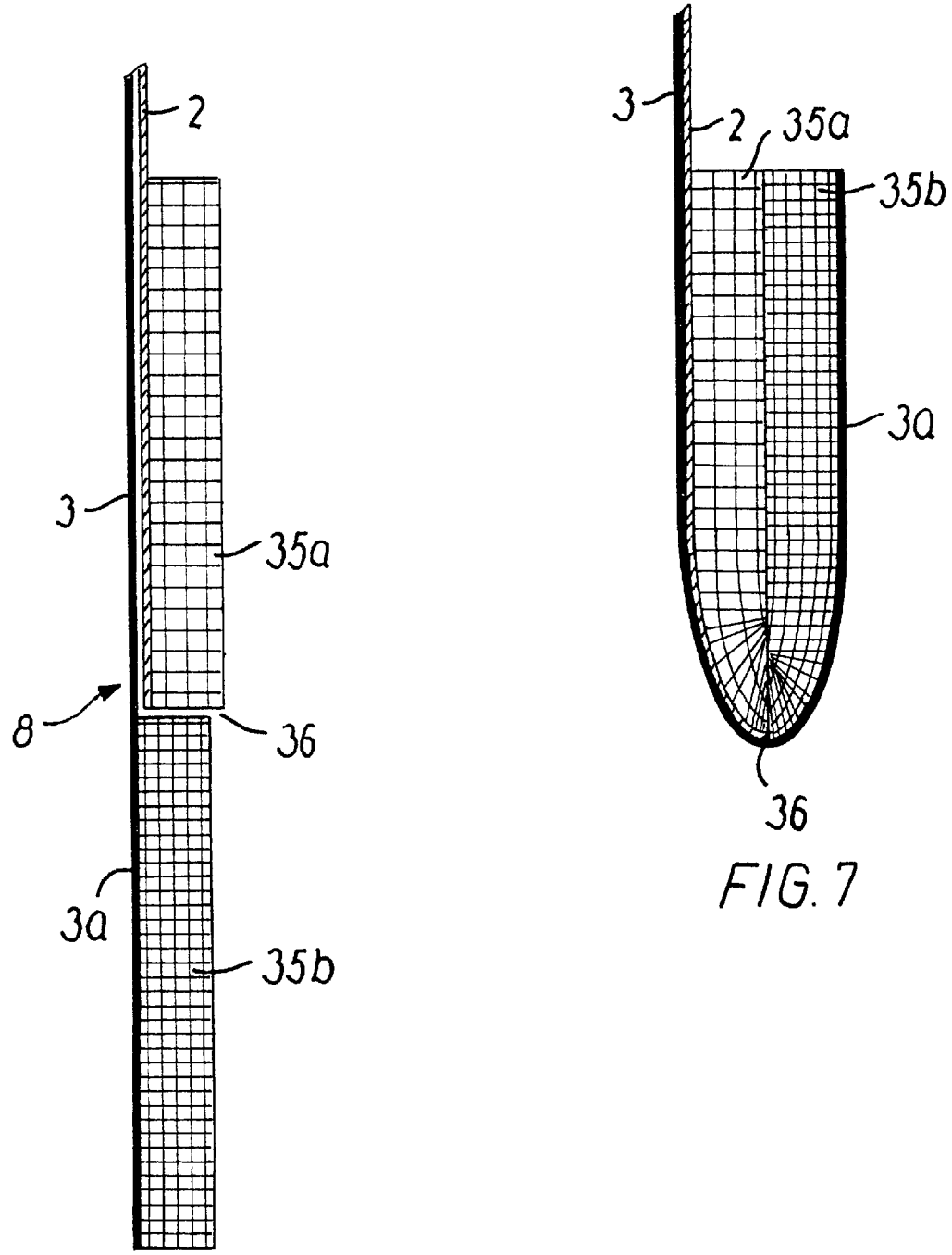

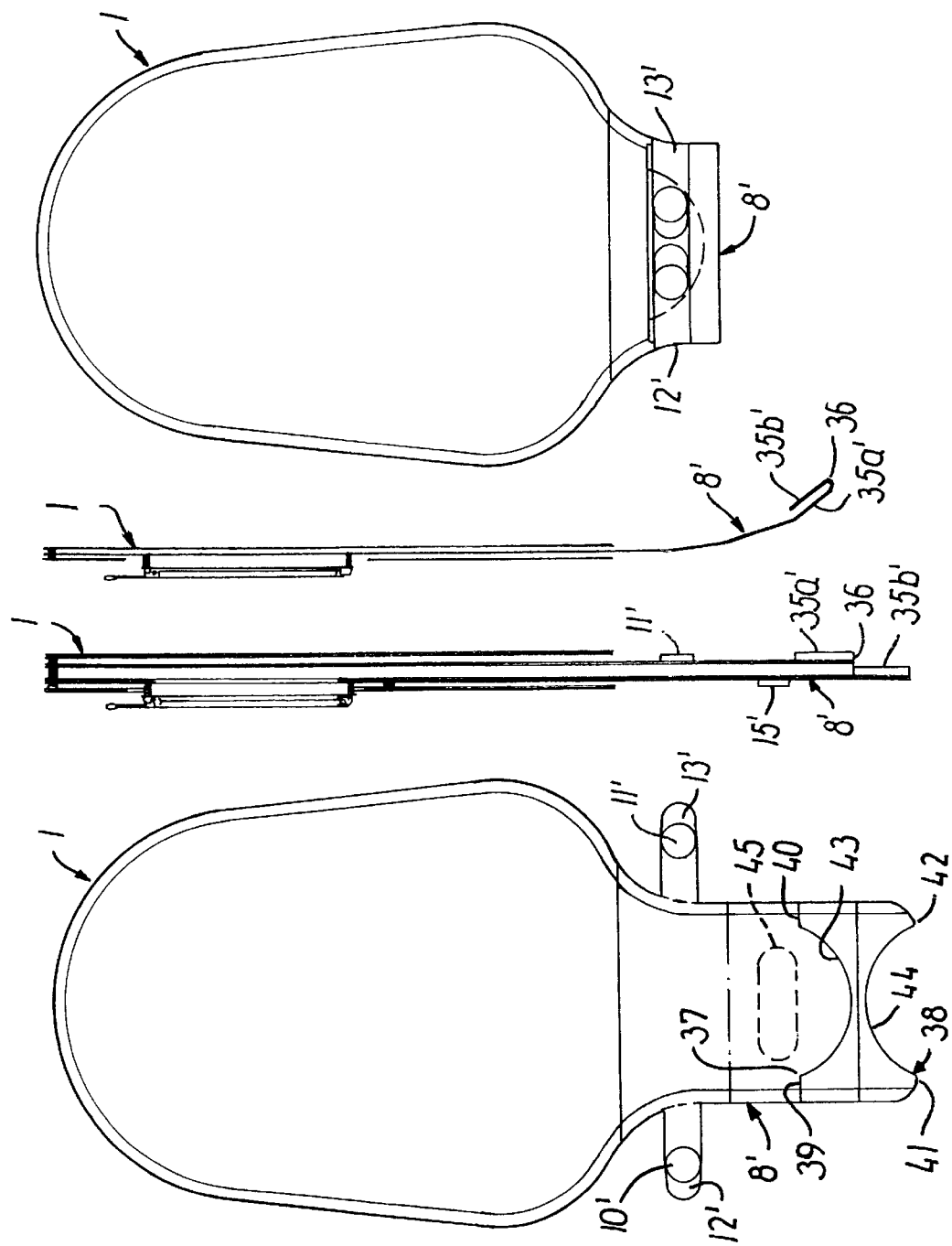

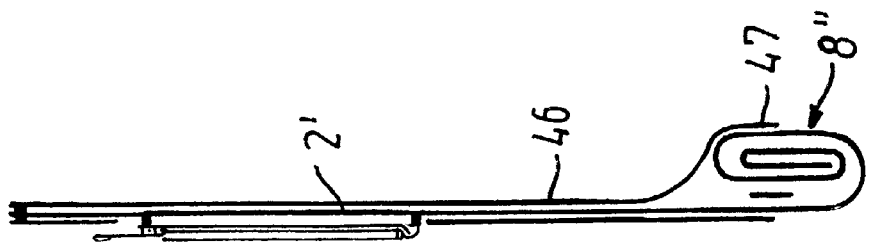
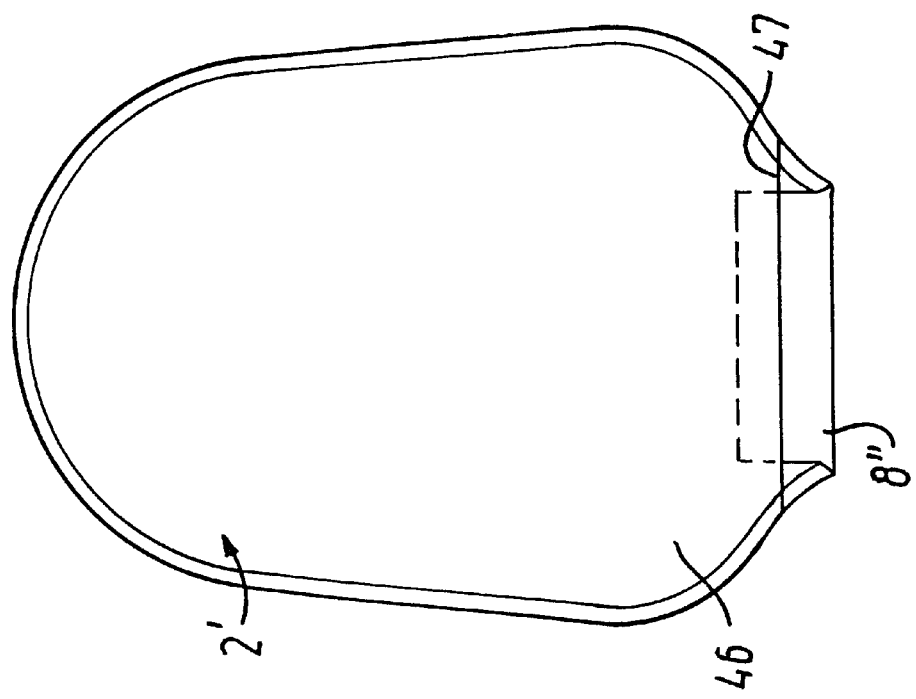

COLLECTING BAG FOR HUMAN BODY WASTES

BACKGROUND OF THE INVENTION.

The invention relates to a collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, said discharge portion being foldable and unfoldable by at least one folding in a longitudinal direction thereof between said distal and proximal ends to bring the discharge portion from an open unfolded condition to a closed folded condition and vice versa, and a locking device being provided at the discharge portion for locking the bag in said closed folded condition of the discharge portion.

This type of drainable collecting bags are often used as ostomy bags. In the case of ileostomy patients and colostomy patients with uncontrolled release of faeces of a more or less fluid consistence, the collecting bag has to be emptied rather frequently, and the closure device thus has to be easy to open and re-close after emptying and at the same time provide a reliable and tight seal in operation, ie. between emptyings.

Several different designs of closure devices have been developed and are generally known.

For instance, GB patent applications Nos. 2 268 065 and 2 000 683 disclose collecting bag with closure devices, in which strips of the interlocking-elements type, such as Velcro, are placed on each of the film blanks of the discharge portion and which after folding the discharge portion tightly are brought into contact with each other.

A further design is shown in EP patent application No. 0 013 109, in which the outlet portion is folded and subsequently tucked into a gap formed by a semi-rigid strip attached to the bag wall.

It is a disadvantage in all of the above designs that accurate and correct handling of the closure device is required in order to provide the necessary seal against leakage in the closed position of the bag. In particular the tight folding of the discharge portion and the tucking operation of the discharge portion in the latter document may cause problems, especially to users having eg. reduced dexterity.

Another type of closure device is shown in published international application No. WO96/19164, in which the discharge portion is rolled up on a locking clip fastened to one of the film blanks. The clip comprises a resilient zone which for instance may be provided as an outer layer of integral foam plastic surrounding a semi-rigid core body. Although the collecting bag and locking clip of this document provide for an improved tightness in comparison with the devices described in the above, the choice of design of the locking device is limited, as the sealing effect is dependent on the locking clip.

BRIEF SUMMARY OF THE INVENTION

With this background, it is the object of the present invention to improve a collecting bag of the kind mentioned in the introduction with respect to security against leakage, easy operation and flexibility regarding the choice of closure device.

For achieving this, a collecting bag according to the invention is characterized in that at least one resilient seal member having greater rigidity than said film blanks is attached to at least one film blank of the discharge portion at or near said discharge opening to engage a contact surface of the other film blank to close the discharge opening in connection with said at least one folding.

By this design, operation of the collecting bag is facilitated as the resilient seal member or members at the discharge opening provide(s) for an efficient sealing of the discharge opening at the beginning and the end of the folding operation during closing and opening, respectively, of the bag, as the discharge opening is substantially fully sealed by the resilience of the member or members. Compared to the collecting bag of WO96/19164, the bag according to the invention offers the advantage that several types of locking devices may be used in connection with the bag.

Advantageous embodiments of the invention are the object of the dependent claims.

BRIEF DESCRIPTION OF THE SEVERAL VIEWS OF THE DRAWING

In the following the invention will be described in further detail with reference to the schematic drawings, in which FIG. 1 shows a plan view of an embodiment of a collecting bag according to the invention, seen from the side intended to face away from the user and in the fully open position;

FIG. 2 shows a longitudinal section of the collecting bag along the line II—II in FIG. 1;

FIG. 3 is a schematic side view diagram of the collecting bag in an intermediate position showing only relevant parts of the bag;

FIGS. 6 and 7 are enlarged schematical cross-sectional views of a distal end part of a discharge portion of the bag in an open and closed condition, respectively;

FIGS. 8 to 11 are views corresponding to FIGS. 1 to 4 of a modification of the discharge portion of the collecting bag in FIG. 1; and FIGS. 12 and 13 are views partly corresponding to FIGS. 4 and 5 of a further modification of the bag.

In FIGS. 2, 3, 5, 9, 10 and 12 some sectional areas are indicated by fully drawn lines in order not to impede the clear reading of the drawings.

Figure 4:
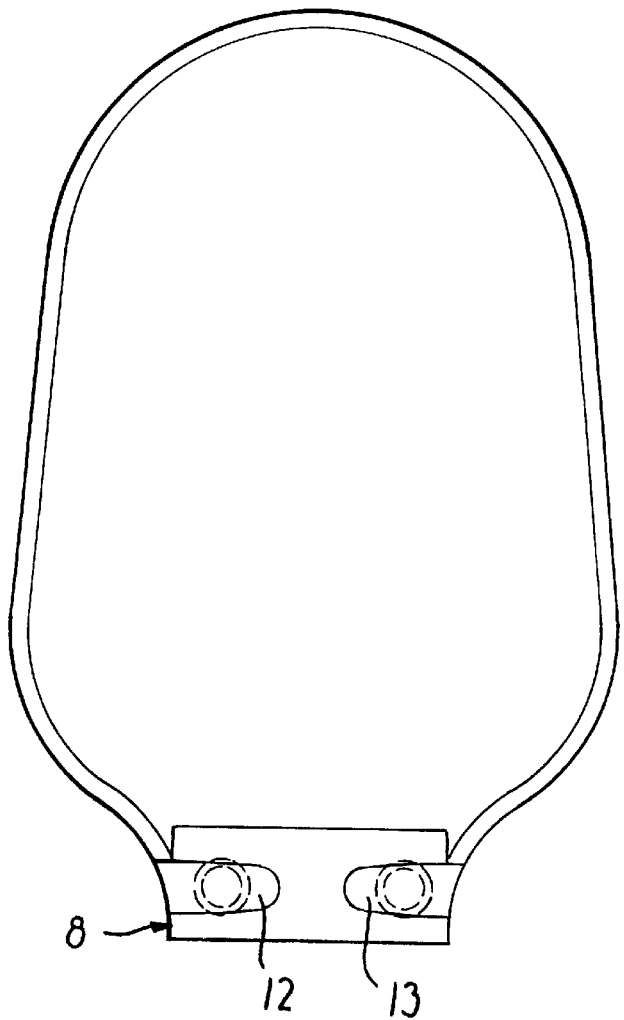
FIG. 4 is a view corresponding to FIG. 1 in the fully closed position of the bag.

DETAILED DESCRIPTION OF THE INVENTION.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The collecting bag shown in the drawings is designed as an ostomy bag of a generally known and common type and comprises a bag member 1 formed by two film blanks 2,3 which are joined along their edges by means of a seam 4 made by welding or in any other convenient manner. The film blanks may be made from any suitable flexible plastic sheet or foil material.

In the film blank 3 which in use is intended to face the user and thus forms the back wall of the bag, an inlet opening 5 is provided which in a manner known per se is surrounded by connecting elements 6 for connection of the bag to a body orifice, ie. in this case an intestinal orifice in the form of a so-called stoma in the user's abdominal wall.

As seen in FIG. 2 a comfort layer 7 of another material than the one used for the film blanks may be provided on the back film blank 3. As further explained in the following both of the two film blanks may alternatively be provided with such a comfort layer which may be made of a conventional non-woven tissue material.

At a distance from the inlet opening 5, the bag is designed with a narrowed, elongated discharge portion 8 starting at a proximal or neck end 8a and extending to a distal or terminal end 8b. The discharge portion 8 is formed by two end sections of the film blanks 2,3 and is likewise joined along opposed side edges 8c and 8d.

In the vicinity of the distal end 8b of the discharge portion 8, a discharge opening 9, through which the bag may be emptied of its contents, is formed by a slit between the two film blanks 2,3 as further explained in the following.

In order to bring the bag from the open or discharge position shown in FIGS. 1 and 2 to a position of use, in which the bag is closed, the collecting bag comprises a locking device which in the embodiment shown comprises foldable locking strips 12 and 13 projecting from the side edges 8c and 8d of the discharge portion 8 at the proximal end 8a thereof. The projecting foldable locking strips 12 and 13 which may be formed integrally with one of the film blanks 2,3 are provide with a first set of locking means 10 and 11, which may comprise male snap fastening members, VELCRO closure members, different types of adhesive members etc. and are releasably engageable with a second set of mating locking means 14 and 15 provided on the back film blank 3 in a manner which will be described in the following. It should be noted that the locking device may be designed in other ways, e.g. as described in applicant's co-pending Danish patent application No. PA 1998 00805, or as a traditional locking clip.

A resilient seal member in the form of a compressible sealing plate 35b is provided on an extension 3a of the back film blank 3 and the front film blank 2 is at its end portion provided with a similar resilient seal member, likewise in the form of a sealing plate 35a. The sealing plates 35a,35b are made from a suitable resilient material, eg. foam, and have a greater rigidity than the film blanks 2 and 3 and extend throughout the width of the discharge portion 8 on either side of the discharge opening 9 which is formed between the extension 3a of film blank 3 and a distal end edge 2a of film blank 2.

As more clearly visible in the enlarged sectional views in FIGS. 6 and 7 the sealing plate 35b is positioned on the surface of the extension 3a facing the discharge opening 9, whereas the sealing plate 35a is positioned on the surface of the front film blank 2 facing away from the discharge opening 9. In the embodiment shown the sealing plates 35a and 35b have the same generally rectangular shape and are arranged with first longitudinal side edges of the two sealing plates facing each other in substantial parallel relationship with a clearance 36 depending on the resilience or compressibility characteristics of the sealing plate and the tensional strength and strechability of the film blanks on which the sealing plates are arranged.

When closing the bag, the discharge portion 8 is folded starting from the distal end by initially folding the sealing plate 35b against the sealing plate 35a using the clearance 36 between them as folding line. As seen in FIG. 7, this initial folding will cause compression of the sealing plates 35a and 35b at least in the parts adjacent the clearance or folding line 36 assisted by the tension of the film blanks 2 and 3 in the folding area, whereby an effectively sealed closure of the discharge opening 9 is provided.

Subsequently, following this initial folding the discharge portion 8 is folded in the embodiment shown two more times until the locking means 14 and 15 are brought into alignment with the projecting locking strips 12 and 13 which are then folded to bring the locking means 10 and 11 into engagement with locking means 14,15.

By using sealing plates 35a, 35b made from a compressible resilient material such as foam, the initial folding of the discharge portion 8 at the discharge opening 9 provides for an improved tightness. Due to the compressibility of the foam material in combination with the squeezing effect from the film material in blanks 2 and 3, particles present in the discharge portion are prevented from moving towards the discharge opening, where such particles might cause formation of flow paths which in turn may give rise to leakage from the bag.

In the embodiment shown, there is a resilient seal member on each film blank and one of these, viz. sealing plate 35b, is provided on the extension 3a of the back film blank 3, such that the resilient members are positioned substantially in extension of each other. This arrangement provides for an optimum functionality of the collecting bag, but other arrangements including the use of only one resilient seal member on only one of the film blanks to engage with a non-resilient contact surface on the other film blank are also conceivable.

When the collecting bag has been in use for some time and is at least partly filled, the bag may be opened by releasing the locking means 10,11 and 14,15 from their mutual engagement, following which the discharge portion 8 may be unfolded and its distal part may be directed into a suitable position, eg. over a toilet. During this operation, the discharge opening 9 may still be maintained in a sealed condition by pressing the sealing plates 35a,35b together. The bag now assumes its open position as shown in FIG. 1 and by releasing the pressure on the sealing plates its contents may be allowed to flow out of the bag.

Subsequently, the user may squeeze the remaining contents out of the bag by stroking or massaging movements in the direction towards the discharge opening 9. When the bag has been emptied, the discharge portion 8 may be thoroughly rinsed.

If desired, the collecting bag may then be closed again by following the closing procedure described in the above.

In the modification of the discharge portion 8' shown in FIGS. 8 to 11 the side edges 37 and 38 of sealing plates 35a' and 35b', respectively, opposite the clearance 36' are composed of edge parts 39, 40 and 41, 42, respectively, adjacent the side edges 8c' and 8d' of the discharge portion 8', which edge parts after the initial folding of sealing plate 35b' into engagement with sealing plate 35a' define the folding line for the subsequent folding of the discharge portion 8'.

Figure 5:
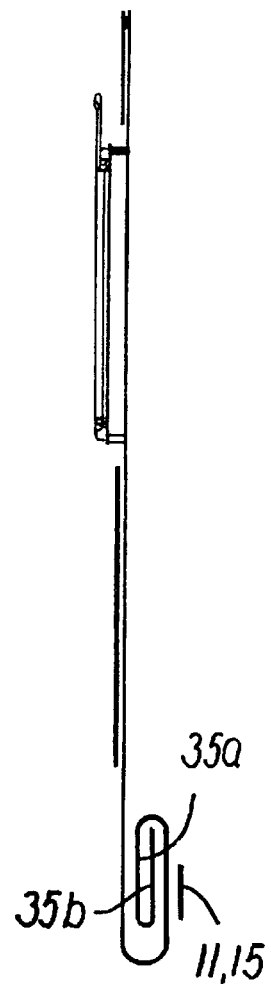
FIG. 5 is a diagram corresponding to FIG. 3 of the collecting bag in the fully closed position.

Between the edge parts 39 and 40 of sealing plate 35a' and between the edge parts 41 and 42 of sealing plate 35b' a relatively large incision is formed defined by a curved contour 43 and 44, respectively. Thereby the surface area of the sealing plates 35a' and 35b' which will need rinsing after emptying the bag through the discharge opening 9', is significantly reduced. Moreover, by this design of the sealing plates the locking means 45, e.g. a VELCRO member is positioned on the discharge portion such that, after folding of the discharge portion, it will be confined within the incision formed by the overlapping curved contours 43, 44 of side edges 37, 38 of the sealing plate 35a', 35b' and the locking strips 12' and 13' with locking means 10', 11' are relocated accordingly. Thereby, compared to the embodiment in FIGS. 1 to 5 the total thickness of the discharge portion 8' in the folded condition will be correspondingly reduced.

In FIGS. 12 and 13 a further modification of the bag is shown in which the front film blank 2' forming the front wall of the bag is covered by a comfort layer 46, e.g. a nonwoven tissue joined with the film blanks 2' and 3' along the contour edges of the bag. Close to the proximal end of the discharge portion 8' a slit 47 is formed between an edge of the comfort layer 46 and the film blank 2'. By a further subsequent folding operation following the folding of the discharge portion 8" to lock the bag by means of the locking device 10"–13" the discharge portion 8" may thereby be located in an at least partly concealed position behind the lower part of the comfort layer 46 adjacent to the slit 47 as more clearly seen in FIG. 13.

The invention should not be regarded as being limited to the embodiments described in the above but various modifications may be carried out without departing from the scope of the following claims.

For example, although the invention has been described only with reference to ostomy bags, it is of course possible to apply it to other forms of collecting bags for human body wastes, such as urinal bags or drainage bags for use in connection with surgery.

What is claimed is:

1. A collecting bag for human body wastes comprising:
    a bag member formed by first and second film blanks with joined edges,
    an inlet opening provided in one of said first and second film blanks,
    connecting elements associated with said inlet opening for connection of the bag to a body orifice,
    an elongated discharge portion starting at a proximal end at a distance from the inlet opening and extending between two end sections of said film blanks to a distal end,
    a discharge opening formed in said discharge portion adjacent said distal end,
    said discharge portion begin foldable and unfoldable by at least one folding in a longitudinal direction thereof between said distal and proximal ends to bring the discharge portion from an open unfolded condition to a closed folded condition and vice versa,
    a locking device provided at the discharge portion for locking the bag in said closed folded condition of the discharge portion,
    a first resilient seal member having greater rigidity than said film blanks attached directly to said first film blank of the discharge portion at or near the discharge opening to engage a contact surface of the second film blank, said contact surface having greater rigidity than said film blanks, to close the discharge opening in connection with said at least one folding,
    said first film blank being formed at the distal end of the discharge portion with an extension beyond a distal edge of the second film blank, said discharge opening being formed between said extension and said distal edge of the second film blank and said first resilient seal member being provided on said extension.

2. A collecting bag according to claim 1, in which said first resilient seal member is designed as a resiliently compressible sealing plate extending transversely to said longitudinal direction of the discharge portion throughout the width of the discharge opening.

3. A collecting bag according to claim 1, in which a second resilient seal member is attached to said second film blank, and said first resilient seal member is provided on a surface of said extension facing said discharge opening, and the second resilient seal member is provided on a surface of said second film blank facing away from said discharge opening.

4. A collecting bag according to claim 3, in which said first and second resilient seal members are first and second resiliently compressible sealing plates, respectively, extending transversely to said longitudinal direction of the discharge portion throughout a width of the discharge opening, and in which said first and second sealing plates are arranged with respective longitudinal side edges thereof facing and extending parallel to each other with a clearance between said first and second sealing plates permitting said at least one folding.

5. A collecting bag according to claim 4, in which said locking device is provided close to the proximal end of said discharge portion to allow folding of said discharge portion by at least one subsequent folding following said at least one folding, a folding line for said at least one folding being defined by the clearance between said first and second sealing plates, and a folding line for said at least one subsequent folding being defined by parallel edge parts of said second sealing plate nearest the proximal end of said discharge portion.

6. A collecting bag according to claim 5, in which side edges of the two sealing plates opposite said first longitudinal side edges have identical contours.

7. A collecting bag according to claim 6, in which in each of said side edges an incision is formed between said edge parts to reduce the surface area of said sealing plates.

8. A collecting bag according to claim 7, in which said locking device comprises foldable locking strips projecting from opposite side edges of the discharge portion and being provided at one surface with first locking means engageable with second locking means provided on a surface part of said discharge portion which after said at least one subsequent folding is located in alignment with said locking strips, and in which said second locking means is positioned on the discharge portion such that in the folded condition thereof it is confined within the incisions in the folded, overlapping sealing plates.

9. A collecting bag according to claim 5, in which said locking device comprises foldable locking strips projecting from opposite side edges of the discharge portion and being provided at one surface with first locking means engageable with second locking means provided on a surface part of said discharge portion which after said at least one subsequent folding is located in alignment with said locking strips.

10. A collecting bag for human body wastes comprising a bag member having a narrowed, elongated discharge portion that includes a discharge opening and two resiliently compressible sealing members adjacent the discharge opening, one sealing member on an upper side thereof in a longitudinal direction and the other sealing member on a lower side thereof such that when said discharge opening is unfolded said two sealing members are side by side and each is adjacent the other along only one edge thereof and positioned substantially in extension of each other in the longitudinal direction, said discharge portion being foldable and unfoldable by at least one folding in the longitudinal direction thereof to bring the discharge portion from an open unfolded condition to a closed, folded condition and vice versa, each of said sealing members extending transversely to said longitudinal direction throughout a width of said discharge opening, such that folding of said discharge portion along a line defined by the adjacent edges of said two sealing members compresses said sealing members at least in parts adjacent said line to provide an effectively liquid-sealed closure of said discharge opening.

11. The collecting bag as set forth in claim 10, wherein said resiliently compressible sealing member is made of foam material.

12. The collecting bag as set forth in claim 10, wherein a clearance between adjacent edges of said two sealing members is parallel with said discharge opening and permits said at least one folding.

13. The collecting bag as set forth in claim 12, further comprising locking strips projecting from opposite side edges of said discharge portion and having a first locking means such that, after the at least one folding along the line followed by a second folding along a longitudinal edge of at least one of said sealing members, said first locking means aligns with a second locking means on a surface portion of said discharge portion to secure the discharge portion in the closed, folded condition.

14. The collecting bag as set forth in claim 12, wherein the collecting bag is made of two film blanks, with each of said two resiliently compressible sealing members being mounted on a respective one of the two film blanks.

* * * * *